(12) United States Patent
Chou et al.

(10) Patent No.: US 7,534,588 B2
(45) Date of Patent: May 19, 2009

(54) METHODS, KITS AND POLYNUCLEOTIDES FOR SIMULTANEOUSLY DIAGNOSING VIRUSES

(75) Inventors: George Chin-Sheng Chou, Tainan County (TW); Sayion Yiyang, Tainan County (TW)

(73) Assignee: AsiaGen Corporation, Tainan County (TW)

( * ) Notice: Subject to any disclaimer, the term of this patent is extended or adjusted under 35 U.S.C. 154(b) by 0 days.

(21) Appl. No.: 11/753,915

(22) Filed: May 25, 2007

(65) Prior Publication Data

US 2008/0293049 A1 Nov. 27, 2008

(51) Int. Cl.
*C12P 19/34* (2006.01)
*C07H 21/04* (2006.01)
*G01N 31/22* (2006.01)

(52) U.S. Cl. ............... 435/91.2; 536/24.33; 536/24.32; 422/61

(58) Field of Classification Search ............ None
See application file for complete search history.

(56) References Cited

U.S. PATENT DOCUMENTS

| | | | | |
|---|---|---|---|---|
| 5,686,272 A | * | 11/1997 | Marshall et al. | 435/91.2 |
| 6,623,920 B1 | * | 9/2003 | Bee et al. | 435/5 |
| 2003/0039955 A1 | * | 2/2003 | Feng et al. | 435/5 |
| 2006/0216693 A1 | * | 9/2006 | Brule et al. | 435/5 |

FOREIGN PATENT DOCUMENTS

| | | | |
|---|---|---|---|
| EP | 1666609 | * | 7/2007 |
| JP | 2003180357 | * | 7/2003 |
| WO | WO/95/35390 | * | 12/1995 |
| WO | WO/03/000839 | * | 1/2003 |
| WO | WO/2005/071401 | * | 8/2005 |
| WO | WO/2006/002547 | * | 1/2006 |

OTHER PUBLICATIONS

Wen et al., "A visual DNA chip for simultaneous detection of hepatitis B virus, hepatitis C virus, and human immunodeficiency virus type-1," Biosensors and Bioelect., 2004, vol. 19, pp. 685-692.*

Trask et al., "Molecular Epidemiology of human immunodeficiency virus type 1 transmission in a heterosexual cohort of discordant couples in Zambia," J. Virol., 2002, vol. 76, No. 1, pp. 397-405.*

Ngui et al., "Selective transmission of hepatitis B virus after percutaneous exposure," J. Infect. Dis., 2000, vol. 181, No. 3, pp. 838-843.*

Buck et al., "Design Strategies and Performance of Custom DNA Sequencing Primers," Biotechniques, Sep. 1999, vol. 27, No. 3, pp. 528-536.*

J.-P. Defoort et al., Simultaneous Detection of Multiplex-Amplified Human Immunodeficiency Virus Type 1 RNA . . . , Journal, Mar. 2000, pp. 1066-1071, vol. 38 No. 3, American Society for Microbiology.

Hitoshi Ohnuma et al., The First Large-Scale Nucleic Acid Amplification Testing (NAT) of Donated Blood Using Multiplex Reagent et al . . . , Journal, 2001, pp. 667-672, Microbiol. Immunol.

* cited by examiner

*Primary Examiner*—Kenneth R. Horlick
*Assistant Examiner*—Molly Baughman
(74) *Attorney, Agent, or Firm*—WPAT P.C.; Anthony King (57) ABSTRACT

The present invention provides a simultaneous method for diagnosing HBV, HCV and HIV of a suspected patient. The present invention further provides different primer sets and specific probes for HBV, HCV and HIV. The present invention also provides a kit for simultaneous diagnosing of HBV, HCV and HIV.

10 Claims, 8 Drawing Sheets

(A) The work conditions of multiplex PCR reaction.

| Reagent | | #1 | #2 | #3 | #4 | #5 | #6 | #7 | #8 | #9 | #10 | #11 | #12 | #13 |
|---|---|---|---|---|---|---|---|---|---|---|---|---|---|---|
| 10µM HBV primer | | 2 | 2 | 2 | 2 | 2 | 2 | 2 | 2 | 2 | 2 | 2 | 0 | 2 |
| 10µM HCV primer | | 1 | 1 | 1 | 1 | 1 | 1 | 1 | 1 | 1 | 1 | 1 | 0 | 1 |
| 10µM HIV primer | | 5 | 5 | 5 | 5 | 5 | 5 | 5 | 5 | 5 | 5 | 5 | 0 | 5 |
| 10× PCR buffer | | 1 | 2 | 3 | 4 | 5 | 6 | 9 | 12 | 15 | 18 | 6 | 6 | 0 |
| 1 mM dNTP | | 6 | 6 | 6 | 6 | 6 | 6 | 6 | 6 | 6 | 6 | 6 | 6 | 6 |
| 60% DMSO | | 8 | 8 | 8 | 8 | 8 | 8 | 8 | 8 | 8 | 8 | 8 | 8 | 8 |
| 25 mM $MgCl_2$ | | 1.6 | 1.6 | 1.6 | 1.6 | 1.6 | 1.6 | 1.6 | 1.6 | 1.6 | 1.6 | 1.6 | 1.6 | 1.6 |
| Thermostable Taq Polymerase (dilute 10×) | | 2 | 2 | 2 | 2 | 2 | 2 | 2 | 2 | 2 | 2 | 2 | 2 | 2 |
| $10^3$ | HBV DNA template | 1 | 1 | 1 | 1 | 1 | 1 | 1 | 1 | 1 | 1 | 0 | 1 | 1 |
| | HCV DNA template | 1 | 1 | 1 | 1 | 1 | 1 | 1 | 1 | 1 | 1 | 0 | 1 | 1 |
| | HIV DNA template | 1 | 1 | 1 | 1 | 1 | 1 | 1 | 1 | 1 | 1 | 0 | 1 | 1 |
| | IC DNA template | 1 | 1 | 1 | 1 | 1 | 1 | 1 | 1 | 1 | 1 | 0 | 1 | 1 |
| DEPC-$H_2O$ | | 29.4 | 28.4 | 27.4 | 26.4 | 25.4 | 24.4 | 21.4 | 18.4 | 15.4 | 12.4 | 28.4 | 32.4 | 30.4 |
| Total Volume | | 60 | 60 | 60 | 60 | 60 | 60 | 60 | 60 | 60 | 60 | 60 | 60 | 60 |

(B) The electrophoresis result of multiplex PCR

```
M: 100~300 bp ladder
#1: 0.17x PCR buffer        #8: 2x PCR buffer
#2: 0.33x PCR buffer        #9: 2.5x PCR buffer
#3: 0.50x PCR buffer        #10: 3x PCR buffer
#4: 0.67x PCR buffer        #11: primer free
#5: 0.83x PCR buffer        #12: template free
#6: 1x PCR buffer           #13: w/o PCR buffer
#7: 1.5x PCR buffer
```

METHODS, KITS AND POLYNUCLEOTIDES FOR SIMULTANEOUSLY DIAGNOSING VIRUSES

FIELD OF THE INVENTION

The present invention relates to kits and methods for detecting various viruses from the samples of a suspected patient. The present invention further relates to polynucleotides for amplifying and identifying different kinds of viruses.

BACKGROUND OF THE INVENTION

Human immunodeficiency virus or HIV is a retrovirus that causes Acquired Immunodeficiency Syndrome (AIDS), a condition in which the immune system begins to fail, leading to life-threatening opportunistic infections.

HIV was classified as a member of the genus lentivirus, part of the family of retroviridae. Lentiviruses are transmitted as single-stranded, positive-sense, enveloped RNA viruses. Upon entry of the target cell, the viral RNA genome is converted to double-stranded DNA by a virally encoded reverse transcriptase that is present in the virus particle. This viral DNA is then integrated into the cellular DNA by a virally encoded integrase so that the genome can be transcribed. Once the virus has infected the cell, two pathways are possible: either the virus becomes latent and the infected cell continues to function, or the virus becomes active and replicates, and a large number of virus particles are liberated that can then infect other cells.

HIV primarily infects vital cells in the human immune system such as helper T cells (specifically CD4+ T cells), macrophages and dendritic cells. HIV infection leads to low levels of CD4+ T cells through three main mechanisms: firstly, direct viral killing of infected cells; secondly, increased rates of apoptosis in infected cells; and thirdly, killing of infected CD4+ T cells by CD8 cytotoxic lymphocytes that recognize infected cells. When CD4+ T cell numbers decline below a critical level, cell-mediated immunity is lost, and the body becomes progressively more susceptible to opportunistic infections. Eventually, most HIV-infected individuals develop AIDS and die; however about one in ten remain healthy for many years, with no noticeable symptoms.

HIV infection in humans is now pandemic. As of January 2006, the Joint United Nations Program on HIV/AIDS (UNAIDS) and the World Health Organization (WHO) estimate that AIDS has killed more than 25 million people since it was first recognized on Dec. 1, 1981, making it one of the most destructive pandemics in recorded history. Furthermore, many people are unaware that they are infected with HIV, and elevate the risk to transmission of this disease. Since donors may therefore be unaware of their infection, donor blood and blood products used in medicine and medical research are routinely screened for HIV.

Another threatening disease, Hepatitis B is a disease of the liver caused by the Hepatitis B virus (HBV), a member of the Hepadnavirus family and one of several unrelated viral species which cause viral hepatitis. It was originally known as "serum hepatitis" and has caused current epidemics in parts of Asia and Africa. HBV is a non-cytopathic virus. This means that the virus, itself, does not cause direct damage to liver cells. Instead, it is the immune system's aggressive response to the virus that usually leads to inflammation and damage to the liver (hepatitis). However, HBV can cause damage to the genetic material inside liver cells. This can lead to liver cancer which, like hepatitis, can also be fatal.

HBV is very similar to HIV in the ways it is transmitted: through direct blood-to-blood contact and through sexual activity. However, blood levels of HBV are much higher than for HIV, making this virus much easier to transmit in certain situations (e.g., from mother to child during delivery).

Like HBV, Hepatitis C virus (HCV) infection causes liver inflammation. The parenteral route of infection seems to be most prevalent, with high rates of infection seen in intravenous drug abusers, haemophiliacs and recipients of unscreened blood transfusions. It has been estimated that 2.2% of the world's population, ~130 million people, are infected with hepatitis C.

HCV is a small (50 nm in size), enveloped, single-stranded, positive sense RNA virus in the family Flaviviridae. HCV mainly replicates within hepatocytes in the liver, although there is controversial evidence for replication in lymphocytes or monocytes. Circulating HCV particles bind to receptors on the surfaces of hepatocytes and subsequently enter the cells. Two putative HCV receptors are CD81 and human scavenger receptor class B1 (SR-BI). However, these receptors are found throughout the body. The identification of hepatocyte-specific cofactors that determine observed HCV liver tropism is currently under investigation As with HBV, chronic HCV infection is a major risk factor for HCC. >80% of the world's 530000 cases of liver cancer per year are caused by viral hepatitis infection, with ~60% associated with HBV and ~40% with HCV. Time from HCV transmission to development of cancer ranges from 10 to 50 years (median 30 years). There is a strong association between chronic HCV infection, cirrhosis, and hepato-carcinogenesis Thus, to prevent disease transmission and diagnosis of HIV, HBV, and HCV, a good way to specifically and quickly detect and identify those viruses is recommended. In most cases, virus identifying consists of initial screening with an enzyme-linked immunosorbent assay (ELISA) to detect antibodies to virus protein. Specimens with a non-reactive result from the initial ELISA are considered negative unless new exposure to an infected partner or partner of unknown infection status has occurred. Specimens with a reactive ELISA result are retested in duplicate. If the result of either duplicate test is reactive, the specimen is reported as repeatedly reactive and undergoes confirmatory testing with a more specific supplemental test (e.g., Western blot or, less commonly, an immunofluorescence assay (IFA)). Only specimens that are repeatedly reactive by ELISA and positive by IFA or reactive by Western blot are considered positive and indicative of virus infection. Specimens that are repeatedly ELISA-reactive occasionally provide an indeterminate Western blot result, which may be either an incomplete antibody response to virus in an infected person or nonspecific reactions in an uninfected person. Although IFA can be used confirm infection in these ambiguous cases, this assay is not widely used. Generally, a second specimen should be collected >1 month later and retested for persons with indeterminate Western blot results. In addition, a few tested specimens might provide inconclusive results because of a low quantity specimen. In these situations, a second specimen is collected and tested for virus infection.

Although less commonly available, nucleic acid testing (e.g., viral RNA or proviral DNA amplification method) can also help diagnosis in certain situations and become more acceptable. The importance of nucleic acid testing (NAT) has become increasingly evident during the last decade for many purposes, such as diagnosing viral infections, monitoring antiviral therapy, and improving the safety of blood supplies. NAT combines the advantages of direct and highly sequence-specific detection of the genome of an infectious agent with an analytic sensitivity that is several orders of magnitude greater than that of antigen detection or virus isolation methods. NAT also reduces the risks of viral transmission during the period between infection and seroconversion, of infection with immunovariant viruses, of immunosilent carriage, and of occult carriage. For example, the risky period of HBV detecting by ELISA-based assay is 45-55 days, HCV is 72 days, and HIV is 22 days. However, when using NAT, the risky period of HBV can be shortened to 35-45 days, HCV can be shorten to 13 days, and HIV can be shortened to 11 days. NAT theoretically cannot eliminate the infection risky period completely, but its application can practically reduce the dangerous transmission of infectious disease.

Unfortunately, the investment cost for instruments, a running cost for reagents, a lack of maintenance support, complex and often labor-intensive procedures that require trained personnel, and the need for cold-chain transport and storage of reagents render NAT unaffordable in the settings where it is needed most. These settings include predominantly the resource-limited countries of Africa, Asia, and Latin America with high prevalence of infectious diseases. Consequently, two complementary approaches to lower the costs of NAT have been proposed: pool testing for large-scale screening and the development of multiplex assays for the simultaneous detection of several infectious agents, as refer to Ohnuma H. et al, Microbiology Immunol.45, p667 (2001) and Defoort J.-P et al, J. Clinical Microbiology. 38, p1066 (2000).

SUMMARY OF THE INVENTION

The present invention relates to kits and methods for simultaneously detecting hepatitis B virus (HBV), hepatitis C virus (HCV), and human immunodeficiency virus (HIV) from the samples of a suspected patient.

This invention also relates to polynucleotides for amplifying and identifying different kinds of viruses.

DETAILED DESCRIPTION OF THE INVENTION

In the present invention, a method has been developed for rapid and sensitive detection HBV, HCV, and HIV. This invention uses a nested PCR and microsphere-based probe that enhance the sensitivity and specificity for the detection of HBV, HCV, and HIV. Further, this invention provides a more convenient method for diagnosing HBV, HCV, and HIV at one time, in which using different primer sets in the same PCR reaction to amplify different target DNA from different virus respectively. In general, the assay system of the invention can reduce the whole process of virus detection, simplify the operation, and lower the costs. Particularly, when it applies to blood and serum screening, the danger of blood transfusion in infectious blood-borne pathogenic viruses, like HBV, HCV, and HIV can be diminished to the lowest.

The present invention relates to a method for identifying HBV (Hepatitis type B virus), HCV (Hepatitis type C virus), and HIV (Human immunodeficiency virus) simultaneously comprises:

(a) amplifying DNA fragments of those viruses synchronously by different primer sets; the outer primer sets used to amplify DNA of a sample consisting of 5'-CGC-GAAGAACCTTACCTGGTTTTGACATG-3' as SEQ ID NO:1 and 5'-GGCAACTAATGACAAGGGT-TGCGCTC-3' as SEQ ID NO:2 for HBV; 5'-CAC-CATAGATCACTCCCCTGTGAGGAAC-3' as SEQ ID NO:3 and 5'-GATGCACGGTCTACGAGACCTC-CCGG-3 as SEQ ID NO:4 for HCV; 5'-CTCTCTGGC-TATCTAGGGAACCCACTGCT-3' as SEQ ID NO:5 and 5'-GCGCCACTGCTAGAGATTTTCCACAC-3' as SEQ ID NO:6 for HIV.

The inner primer sets used to amplify DNA of a sample consisting of 5'-CATGTCCTACTGTTCAAGCCTC-3' as SEQ ID NO:7 and 5'-CCCGATACAGAGCTGAGGCGG-TATC-3' as SEQ ID NO:8 for HBV; 5'-GCGTTAGTAT-GAGTGTCGTGCAGCC-3' as SEQ ID NO:9 and 5'-GCAC-CCTATCAGGCAGTACCACAAG-3' as SEQ ID NO:10 for HCV; 5'-TTAAGCCTCAATAAAGCTTG-3' as SEQ ID NO:11 and 5'-AATGGTCTGAGGGATCTC-3' as SEQ ID NO:12 for HIV.

(b) hybridizing the amplified DNA fragments with different specific probes; probe for identifying amplified DNA fragments respectively from HBV, HCV, or HIV consisting of: 5'-AAGCCACCCAAGGCACAGCTT-3' as SEQ ID NO: 13 for HBV; 5'-CGAGTAGTGT-TGGGTCGCGAAAGGC-3' as SEQ ID NO: 14 for HCV; and 5'-TTTTTTTTTTGTCACACAACA-GATGGGCAC-3' as SEQ ID NO: 15 for HIV.

(c) detecting the hybrid products of (b).

The method of present invention can be applied in many microorganisms including virus, bacteria, fungi etc. Particularly, this invention of using multiplex assay has been established for HBV, HCV and HIV, which are three blood-borne pathogenic viruses of major epidemiological and clinical importance. Using this method, those viruses can be detected at one time. In this way, the detection time can be shorten and get the results quickly.

In general, any body fluid such as CSF, serum, blood, sputum, pleural effusion, throat swab and stools can be used in the clinical tests. The preferred samples for this invention are from CSF, serum, blood, sputum, pleural effusion, and throat swab.

The polymerase chain reaction (PCR) and other forms of target amplification have enabled rapid advances in the development of powerful tools for detecting and quantifying specific DNA sequence of interest for research, forensic and clinical applications. As used herein, RT-PCR (reverse transcription polymerase chain reaction) is a technique for amplifying a defined piece of a ribonucleic acid (RNA) molecule extracted from clinical samples. The RNA strand is first reverse transcribed into its DNA complement or complementary DNA, followed by amplification of the resulting DNA using polymerase chain reaction.

To ensure the specificity of PCR, the nested PCR is further performed in this method. Nested PCR means that two pairs of PCR primer were used for a single locus. The first primer pair, also called outer primers, was performed in RT-PCR to amplify the target locus. The second pair of primers (nested, inner primers) binds within the first PCR product and produces a second PCR product that will be shorter than the first one. The logic behind this strategy is that if the wrong locus were amplified by mistake, the probability is very low that it would also be amplified a second time by a second pair of primers.

The designation of the primer and the probe comprises several steps described as follows:

The process for designing different primer set which is used to amplify DNA fragments of various viruses respectively: (a) selecting a conserved and stable region from various virus genomes respectively; (b) selecting a target fragment from the conserved and stabled, having the sequence are characteristic and specific for identifying the various virus; (c) choosing the sequence in two ends of the target fragment to be outer primers; and selecting another two sequence inside the target fragment to be inner primers used for second PCR run; (d) analyzing the chosen primer set along with other varied viruses genomes to avoid nonspecific identifying; (e) analyzing the chosen primer set along with other varied chosen primer sets from different virus genome to avoid primer dimmer or hairpin; (f) choosing a part of the target fragment defined by inner primers to be a probe which is specific to the selected virus; (g) analyzing the chosen probe along with other varied viruses genomes to avoid nonspecific identifying; (h) analyzing the chosen probes and primer sets all together to avoid primer dimmer of hairpin.

The steps of selecting and analyzing process are by use of bio-information software Vector NTI, DNAsis Max, and Array Designer. The software applied to help the primer and probe design, which is not only for specifically target to wanted region, but also to avoid primers and probe inside of them having any complementary binding. One phenomenon of them is hairpin, which refers to a stem and loop association of nucleotides with a palindromic sequence that causes them to form hydrogen bonds with their complementary nucleotides on the same strand.

Nucleic acid amplification reagents include reagents which are well known and may include, but are not limited to, an enzyme having at least polymerase activity, enzyme cofactors such as magnesium or manganese; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

Certain criteria as follows are concerned in amplification conditions. It is well known that annealing is dependent in a rather predictable manner on several parameters, including temperature, ionic strength, sequence length, complementarities, and G: C content of the sequences. For example, lowering the temperature in the environment of complementary nucleic acid sequences promotes annealing. For any given set of sequences, melt temperature, or Tm, can be estimated by any of several known methods. Typically, diagnostic applications utilize hybridization temperatures that are about 10° C. (e.g, 2° C. to 18° C.) below the melt temperature. Ionic strength or "salt" concentration also impacts the melt temperature, since small cations tend to stabilize the formation of duplexes by negating the negative charge on the phosphodiester backbone. Typical salt concentrations depend on the nature and valiancy of the cation but are readily understood by those skilled in the art. Similarly, high G:C content and increased sequence length are also known to stabilize duplex formation because G:C pairings involve 3 hydrogen bonds where A:T pairs have just two, and because longer sequences have more hydrogen bonds holding the sequences together. Thus, a high G:C content and longer sequence lengths impact the hybridization conditions by elevating the melt temperature.

The amplification product produced as above can be detected during or subsequently to the amplification of the target sequence. Gel electrophoresis can be employed to detect the products of an amplification reaction after its completion. Alternatively, one or more of the primers used in the amplification reactions can be labeled so that an amplicon can be directly detected by conventional techniques subsequently. For example, amplification products are hybridized to probes then separated from other reaction components and detected using micro-particles and labeled probes. In recently, many detection techniques have been developed, and their quantifications are generally achieved by measuring the specifically activity of the labeled capture probe, in which enzymes are often employed as biocatalytic labels for the amplified detection of DNA-sensing events.

As used here in, a "probe" is a substance that can be specifically recognized by a particular target. Generally, probes will be solid support to facilitate the separation of DNA. In the present invention, the probes linked to microsphere beads are preferred. Microsphere beads covalently coupled to amine-containing oligonucleotides through their surface carboxylate groups. The small size allows the microsphere beads to remain in suspension for several hours, which is more sufficient for assay setup and analysis, and also provides near-fluid-phase reaction kinesis.

Commonly employed labels include, but are not limited to, biotin, fluorescent molecules, radioactive molecules, chromogenic substrates, chemi-luminescence, and the like. In this present invention, the nucleic acid or oligonucleotide labeled biotin are preferred. When biotin is employed, it is detected by avidin, streptavidin or the like, which is conjugated to a detectable marker, such as an enzyme (e.g., horseradish peroxidase).

For convenient utilization, the primers and probes are labeled with detectable component or molecules. The probe is labeled with a microsphere particle, become a microsphere probe. The primer, including forward primer, reverse primer or both, is labeled by a bioactive component such as biotin. The amplified DNA product hybridized with microsphere probe to form a hybrid complex, and the hybrid complex can be easily separated from unbound DNA products by using centrifugation. The hybrid complex can be further quantitative by using the labeled primer. For example, if the primer is labeled with biotin, adding avidin, the substrate of biotin, into the isolated hybrid complex. The hybrid complex can be further quantified by reading luminescence by Luminometer.

The present invention further provides a primer set for amplifying DNA fragments respectively from HBV (Hepatitis type B virus), HCV (Hepatitis type C virus), and HIV (Human immunodeficiency virus) comprising:

(a) The outer primer sets used to amplify DNA of a sample consisting of SEQ ID NO:1 and SEQ ID NO:2 for HBV;

SEQ ID NO:3 and SEQ ID NO:4 for HCV; SEQ ID NO:5 and SEQ ID NO:6 for HIV.

(b) The inner primer sets used to amplify DNA of a sample consisting of SEQ ID NO: 7 and SEQ ID NO: 8 for HBV; SEQ ID NO: 9 and SEQ ID NO: 10 for HCV; SEQ ID NO: 11 and SEQ ID NO: 12 for HIV. The primer set of the present invention is designed from a conserved and stable region in HBV, HCV and HIV genome respectively. In the present embodiment, the primer is labeled to a bioactive component (such as biotin.)

The present invention also provides a probe for identifying an amplified DNA fragment from HBV, HCV, and HIV consisting of SEQ ID NO: 13 for HBV, SEQ ID NO: 14 for HCV and SEQ ID NO: 15 for HIV. The probe is labeled with a microsphere particle.

Figure 1:
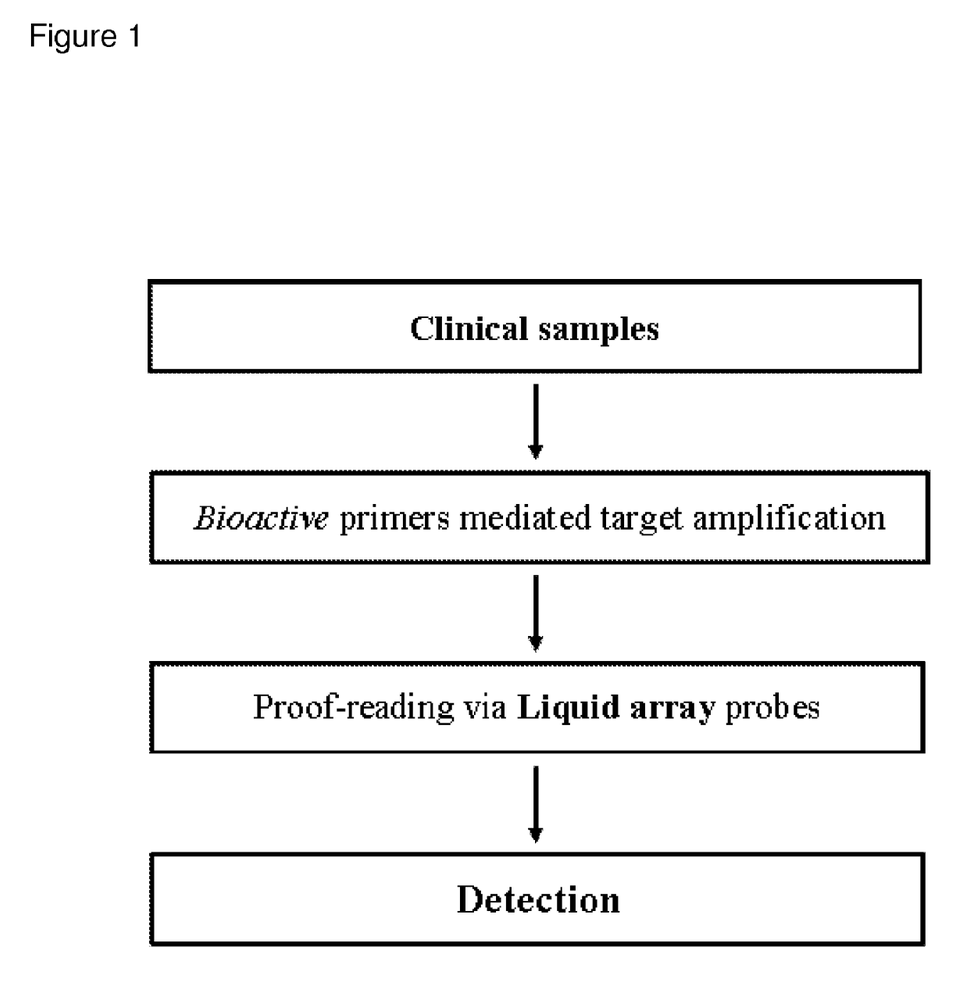
FIG. 1 shows the outline of the detection method of invention.

The process of utilizing the kit for diagnosis of HBV, HCV and HIV simultaneously as described as follows; obtaining the proper sample from patient, in clinical, or any source containing the virus; amplifying the target DNA fragments from the treated sample by using the biotin-labeled primer set; adding the microsphere probe specific to HBV, HCV and HIV respectively into the amplified products to hybridize the specific target; using centrifugation to isolate the hybrid complex and separate unbound amplified products; confirming the hybrid complex by adding avidin-Horse radish peroxidase and its substrate, and reading the luminescence by Luminometer. A luminometer is used to detect and measure luminescence that normally comes from chemical or biological reactions. This process can be referred to FIG. 1.

In one embodiment of the present invention, a kit for detecting HBV, HCV, and HIV comprising:
(a) The outer primer sets used to amplify DNA of a sample consisting of SEQ ID NO:1 and SEQ ID NO:2 for HBV; SEQ ID NO:3 and SEQ ID NO:4 for HCV; SEQ ID NO:5 and SEQ ID NO:6 for HIV.
(b) The inner primer sets used to amplify DNA of a sample consisting of SEQ ID NO: 7 and SEQ ID NO: 8 for HBV; SEQ ID NO: 9 and SEQ ID NO: 10 for HCV; SEQ ID NO: 11 and SEQ ID NO: 12 for HIV.
(c) Probes used to identify the amplified DNA fragment comprising SEQ ID NO: 13 for HBV, SEQ ID NO: 14 for HCV and SEQ ID NO: 15 for HIV.

The primer is labeled with biotin, and the probe is labeled with a microsphere particle as a microsphere probe. The kit further comprises hybridization buffer, washing buffer, and blocking buffer. These buffers are easily purchased form commercial products such as those of Pierce, Biolab, Qiagen etc.

EXAMPLES

Material and Methods
Major kit A: (50 reactions/kit, store in room temperature).
(1) Hybridization buffer (1500 µl per bottle, 2 bottles).
Major kit B: (50 reactions/kit, store in 2~8° C.).
(1) Detection solution (1500 µl per bottle, 2 bottles). SA-PE.
(2) Microsphere probe (180 µl per bottle, 1 bottle).
HBV, HCV, and HIV probe, microsphere beads number: 3, 7, 9

```
HIV probe (SEQ ID NO: 15):
amin-TTTTTTTTTTGTCACACAACAGATGGGCAC

HBV probe (SEQ ID NO: 13):
amin-AAGCCACCCAAGGCACAGCTT

HCV probe (SEQ ID NO: 14):
amin-CGAGTAGTGTTGGGTCGCGAAAGGC
```

Major kit C: (50 reactions/kit, store in −20±5° C.)
(1) Nucleotide amplification solution 1 (420 µl per bottle, 5 bottles, store in −20±5° C.)

```
DEPC, H₂O
HBV outer forward primer (5 µM)
ATGCAACTTTTTCACCTCTGC

HBV outer reverse primer (5 µM)
GGAGACTCTAAGGCTTCCCGA

HCV outer forward primer (5 µM)
CACCATAGATCACTCCCCTGTGAGGAAC

HCV outer reverse primer (5 µM)
GATGCACGGTCTACGAGACCTCCCGG

HIV outer forward primer (5 µM)
CTCTCTGGCTATCTAGGGAACCCACTGCT

HIV outer reverse primer (5 µM)
GCGCCACTGCTAGAGATTTTCCACAC 10x polymerase buffer dNTP (A `U `C `G) (10 mM)

MgCl₂ (25 mM)
```

(2) Nucleotide amplification solution 2 (420 µl per bottle, 5 bottles, store in −20±5° C.)

```
DEPC, H₂O
HBV inner forward primer (5 µM)
biotin-CATGTCCTACTGTTCAAGCCTC

HBV inner reverse primer (5 µM)
CCCGATACAGAGCTGAGGCGGTATC

HCV inner forward primer (5 µM)
biotin-GCGTTAGTATGAGTGTCGTGCAGCC

HCV inner reverse primer (5 µM)
GCACCCTATCAGGCAGTACCACAAG

HIV inner forward primer (5 µM)
biotin-TTAAGCCTCAATAAAGCTTG

HIV inner reverse primer (5 µM)
AATGGTCTGAGGGATCTC 10x polymerase buffer dNTP (A `U `C `G)

MgCl₂ (25 mM)
```

(3) Reverse transcriptase (5.5 µl per bottle, 1 bottles, store in −20±5° C.)
(4) RNase inhibit enzyme (27 µl per bottle, 1 bottles, store in −20±5° C.)
(5) Polymerase (11 µl per bottle, 1 bottles, store in −20±5° C.)

Example 1

Analysis of Nucleotide Sequence and Design of Primers and Probes

Collected and integrated the genomic sequence already identified, and compared and analyzed by use of bio-information software Vector NTI, DNAsis Max, and Array Designer, in order to find a conserved and stable region from various virus genomes respectively. In this region, it is considered to select and design a target fragment as primer or probe having the sequences which are characteristic and specific for identifying the various viruses respectively. Analyzed and cross compared the chosen probes and primer sets all together to avoid primer dimmer or hairpin. Further, the step was needed to check the chosen probe and primer sets along with other varied viruses genomes to avoid nonspecific identifying.

Example 2

Established and Optimized of Nuclei Acid Amplification 2.1 First, established the PCR condition in single virus detection: Established the single virus sensitivity analysis and compared parallel with real time PCR, using the same serum sample to quantify. This sample could be further used as a control for clinical sample sensitivity analysis. In these experiments, the reverse transcriptions reacted in the same condition 2.2 Established the internal standard: This step was used to confirm and distinguish between the negative and pseudo-positive results. The quantified internal standard put into the serum sample had been through the process of extraction, reverse transcription, and nuclei acid amplification, in order to coordinate with the best reaction condition of three pathogenic viruses.

Figure 2:
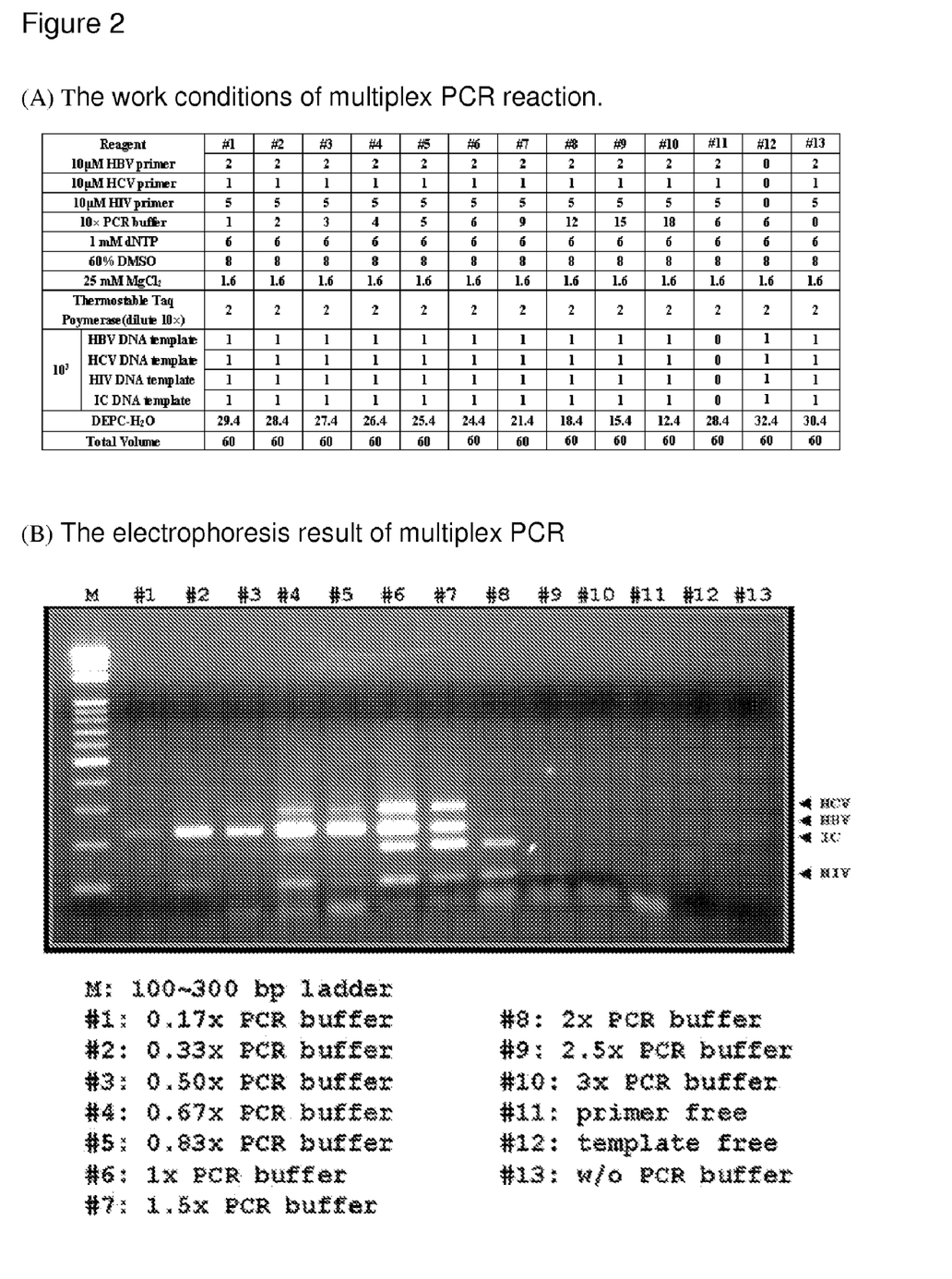
FIG. 2 shows part (A) the work conditions of multiplex PCR reaction and part (B) the electrophoresis result of multiplex PCR.

2.3 Established multiplex PCR, and integrated it into a triad kit: The extension buffer, Taq from different suppliers, primer annealing temperature and primer ratio in the mixture all took into evaluation in order to have the most product of nuclei acid amplification, and not have the production of non specific fragments. The multiplex PCR condition and its test result were shown in FIG. 2.

Example 3

Test and Study the Optimum Conditions of Multiple Nuclei Acid Probes and Hybridized Reactions This kit was based on liquid hybridized reaction, and its advantage is within 15 minutes the reaction can be accomplished over 90%. The major affected factors of hybridized reaction was under investigation, including the salt concentration, kinds and concentration of detergents, reaction temperature, and reaction time, combined these four factors with the probes to see whether there are cross interferences or signals. Test of the diluted detection buffer to lower down the number of kit need, ad stored SA-PE in this dilution buffer. This work was aimed to finish the hybridized reaction results to the high signal (MFI>100, positive/background≧5) and low background (MFI<100).

Example 4

Figure 3:
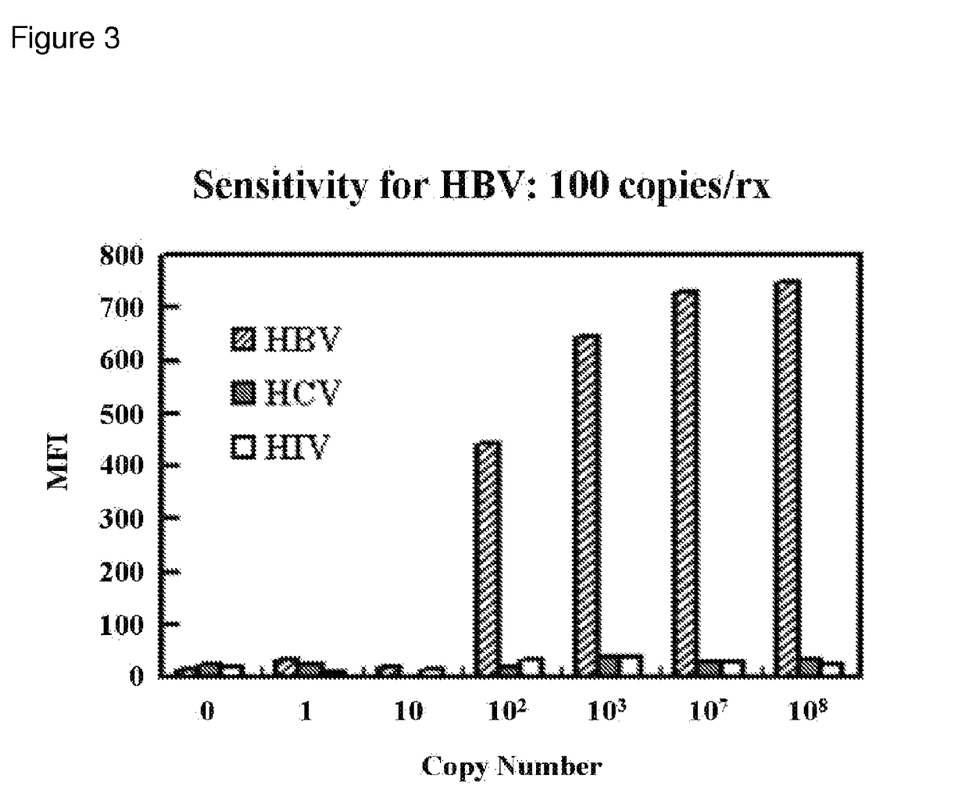
FIG. 3 shows the identification of HBV by the assay of the invention and test its sensitivity to HBV.
Figure 4:
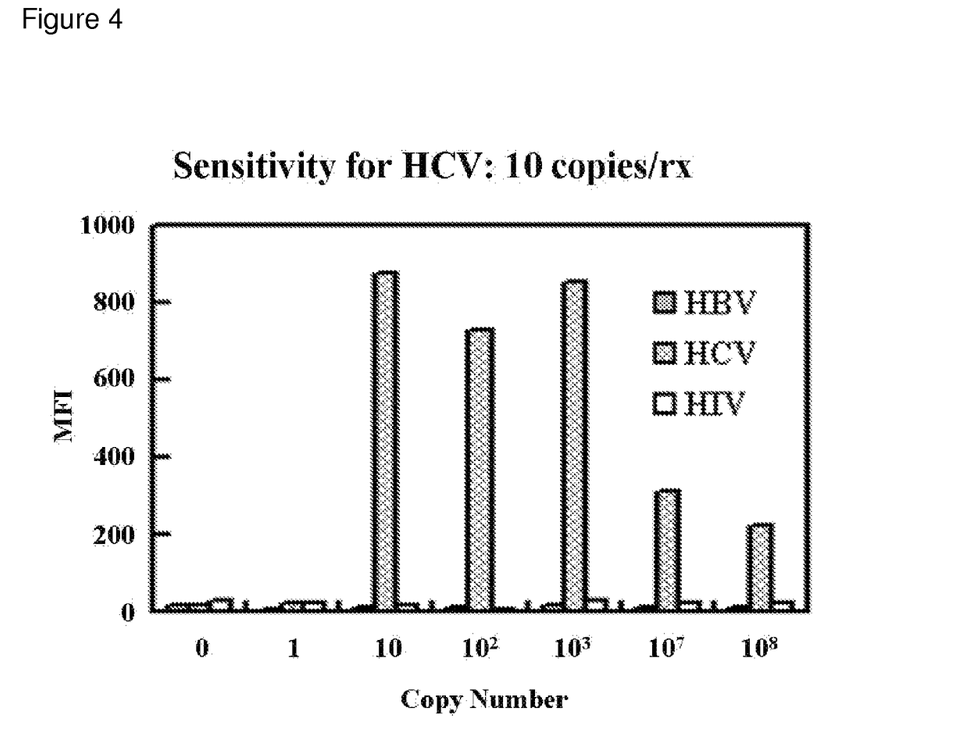
FIG. 4 shows the identification of HCV by the assay of the invention and test of its sensitivity to HCV.
Figure 5:
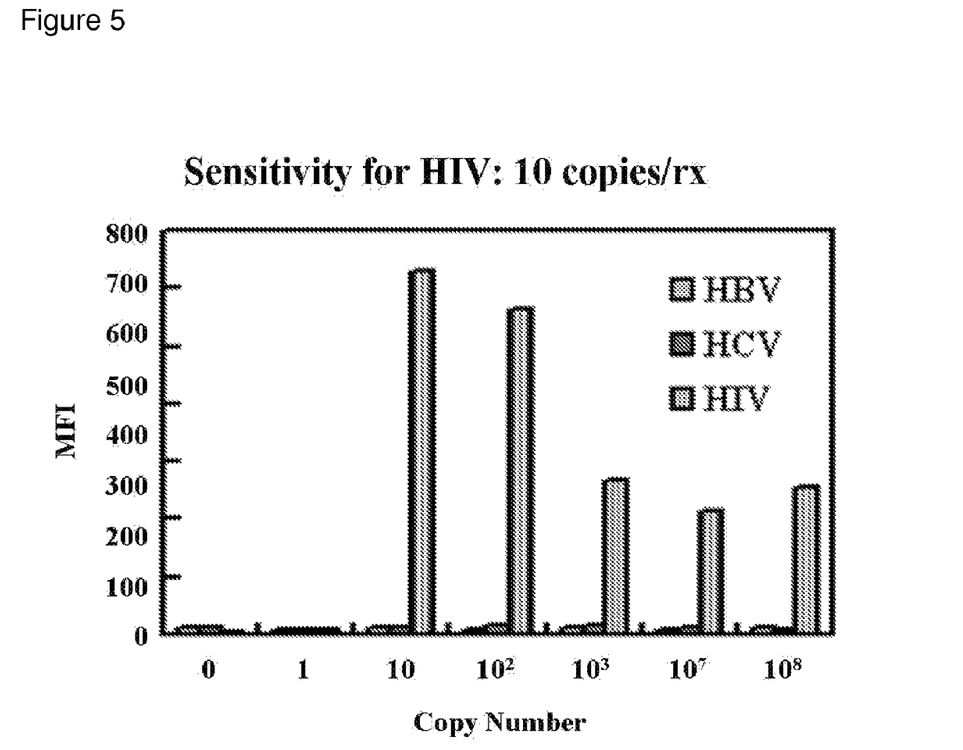
FIG. 5 shows the identification of HIV by the assay of the invention and test its sensitivity to HIV.

Test the Sensitivity of Virus Detection in Assay System, and Integrated the Process of Reagents Operation Test the sensitivity of virus detection in this assay system, in order to find the lowest concentration of virus can be detected. As shown in FIGS. 3, 4 and 5, the sensitivity of HBV can be up to 100 copies/Rx, HCV can be up to 10 copies/Rx, and HIV can be up to 10 copies/Rx. Using high efficiency and operation convenience as the principles to integrate the components of reagents and operation process, this was served for the clinical sample test.

Example 5

Test Clinical Samples and Calibrate the Assay System

Figure 6:
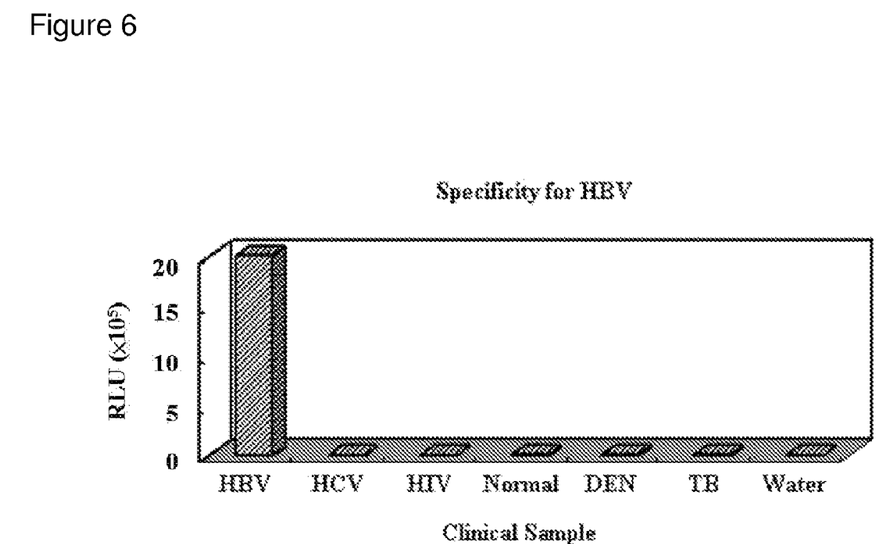
FIG. 6 shows the specificity of this assay to identify HBV. HBV: The hepatitis B virus positive serum; HCV: The hepatitis C virus positive serum; HIV: The human immunodeficiency virus positive serum; DEN: The RNA of Dengue fever virus; TB: *M. tuberculosis*, ATCC27294.
Figure 7:
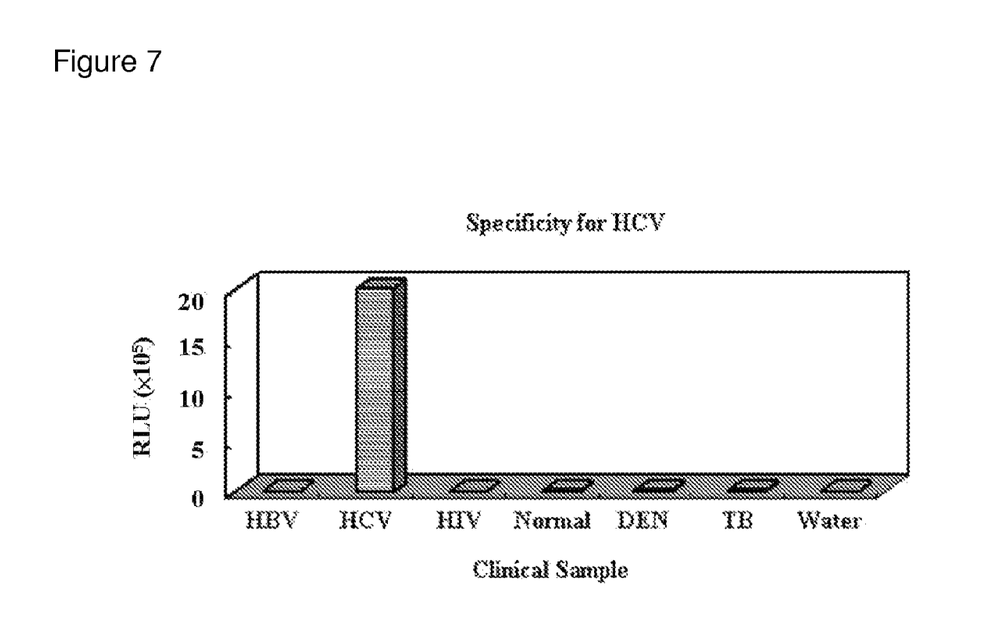
FIG. 7 shows the specificity of this assay to identify HCV. HBV: The hepatitis B virus positive serum; HCV: The hepatitis C virus positive serum; HIV: The human immunodeficiency virus positive serum; DEN: The RNA of Dengue fever virus; TB: *M. tuberculosis*, ATCC27294.
Figure 8:
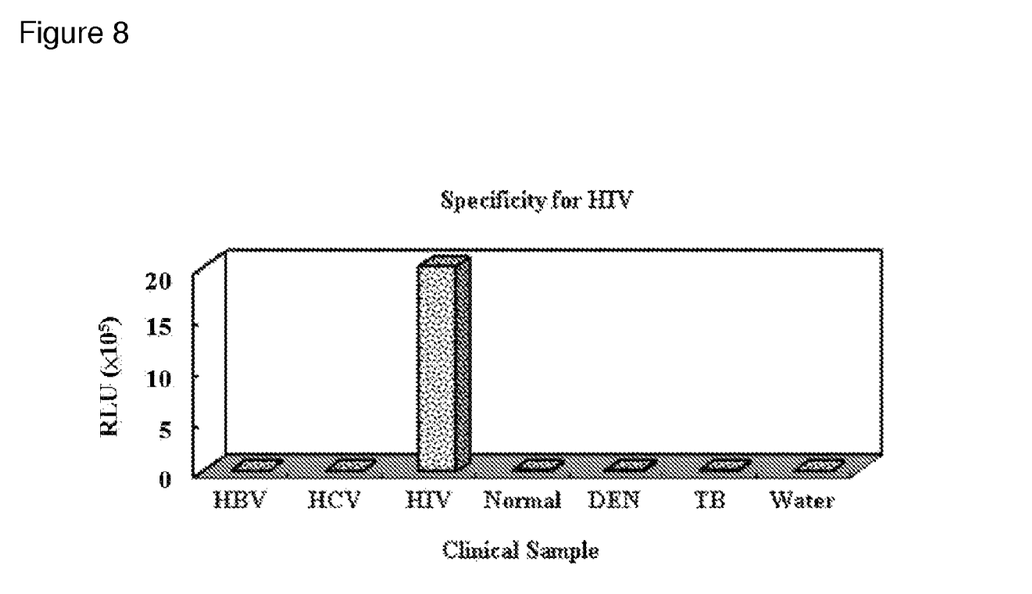
FIG. 8 shows the specificity of this assay to identify HIV. HBV: The hepatitis B virus positive serum; HCV: The hepatitis C virus positive serum; HIV: The human immunodeficiency virus positive serum; DEN: The RNA of Dengue fever virus; TB: *M. tuberculosis*, ATCC27294.

Employed the clinical test, and used this test result to calibrate the assay system, in order to fit the safety requirements of blood screening. As shown in FIGS. 6, 7, and 8, the test of clinical samples had presented the specificity of HBV, HCV, and HIV respectively.

SEQUENCE LISTING

<110> CHOU, George, CHIN-SHENG

SEQUENCE LISTING

<160> NUMBER OF SEQ ID NOS: 15

<210> SEQ ID NO 1
<211> LENGTH: 21
<212> TYPE: DNA
<213> ORGANISM: Artificial sequence
<220> FEATURE:
<223> OTHER INFORMATION: HBV outer forward primer
<220> FEATURE:
<221> NAME/KEY: misc_binding
<222> LOCATION: (1)..(21)

<400> SEQUENCE: 1
atgcaacttt ttcacctctg c                                        21

<210> SEQ ID NO 2
<211> LENGTH: 21
<212> TYPE: DNA
<213> ORGANISM: Artificial sequence
<220> FEATURE:
<223> OTHER INFORMATION: HBV outer reverse primer
<220> FEATURE:

```
<221> NAME/KEY: misc_binding
<222> LOCATION: (1)..(21)

<400> SEQUENCE: 2
ggagactcta aggcttcccg a                                             21

<210> SEQ ID NO 3
<211> LENGTH: 28
<212> TYPE: DNA
<213> ORGANISM: Artificial sequence
<220> FEATURE:
<223> OTHER INFORMATION: HCV outer forward primer
<220> FEATURE:
<221> NAME/KEY: misc_binding
<222> LOCATION: (1)..(28)

<400> SEQUENCE: 3
caccatagat cactcccctg tgaggaac                                      28

<210> SEQ ID NO 4
<211> LENGTH: 26
<212> TYPE: DNA
<213> ORGANISM: Artificial sequence
<220> FEATURE:
<223> OTHER INFORMATION: HCV outer reverse primer
<220> FEATURE:
<221> NAME/KEY: misc_binding
<222> LOCATION: (1)..(26)

<400> SEQUENCE: 4
gatgcacggt ctacgagacc tcccgg                                        26

<210> SEQ ID NO 5
<211> LENGTH: 29
<212> TYPE: DNA
<213> ORGANISM: Artificial sequence
<220> FEATURE:
<223> OTHER INFORMATION: HIV outer forward primer
<220> FEATURE:
<221> NAME/KEY: misc_binding
<222> LOCATION: (1)..(29)

<400> SEQUENCE: 5
ctctctggct atctagggaa cccactgct                                     29

<210> SEQ ID NO 6
<211> LENGTH: 26
<212> TYPE: DNA
<213> ORGANISM: Artificial sequence
<220> FEATURE:
<223> OTHER INFORMATION: HIV outer reverse primer
<220> FEATURE:
<221> NAME/KEY: misc_binding
<222> LOCATION: (1)..(26)

<400> SEQUENCE: 6
gcgccactgc tagagatttt ccacac                                        26

<210> SEQ ID NO 7
<211> LENGTH: 22
<212> TYPE: DNA
<213> ORGANISM: Artificial sequence
<220> FEATURE:
<223> OTHER INFORMATION: HBV inner forward primer
<220> FEATURE:
<221> NAME/KEY: misc_binding
<222> LOCATION: (1)..(22)

<400> SEQUENCE: 7
```

-continued catgtcctac tgttcaagcc tc                                                22

<210> SEQ ID NO 8
<211> LENGTH: 25
<212> TYPE: DNA
<213> ORGANISM: Artificial sequence
<220> FEATURE:
<223> OTHER INFORMATION: HBV inner reverse primer
<220> FEATURE:
<221> NAME/KEY: misc_binding
<222> LOCATION: (1)..(25)

<400> SEQUENCE: 8
cccgatacag agctgaggcg gtatc                                             25

<210> SEQ ID NO 9
<211> LENGTH: 25
<212> TYPE: DNA
<213> ORGANISM: Artificial sequence
<220> FEATURE:
<223> OTHER INFORMATION: HCV inner forward primer
<220> FEATURE:
<221> NAME/KEY: misc_binding
<222> LOCATION: (1)..(25)

<400> SEQUENCE: 9
gcgttagtat gagtgtcgtg cagcc                                             25

<210> SEQ ID NO 10
<211> LENGTH: 25
<212> TYPE: DNA
<213> ORGANISM: Artificial sequence
<220> FEATURE:
<223> OTHER INFORMATION: HCV inner reverse primer
<220> FEATURE:
<221> NAME/KEY: misc_binding
<222> LOCATION: (1)..(25)

<400> SEQUENCE: 10
gcaccctatc aggcagtacc acaag                                             25

<210> SEQ ID NO 11
<211> LENGTH: 20
<212> TYPE: DNA
<213> ORGANISM: Artificial sequence
<220> FEATURE:
<223> OTHER INFORMATION: HIV inner forward primer
<220> FEATURE:
<221> NAME/KEY: misc_binding
<222> LOCATION: (1)..(20)

<400> SEQUENCE: 11
ttaagcctca ataaagcttg                                                   20

<210> SEQ ID NO 12
<211> LENGTH: 18
<212> TYPE: DNA
<213> ORGANISM: Artificial sequence
<220> FEATURE:
<223> OTHER INFORMATION: HIV inner reverse primer
<220> FEATURE:
<221> NAME/KEY: misc_binding
<222> LOCATION: (1)..(18)

<400> SEQUENCE: 12
aatggtctga gggatctc                                                     18

-continued

```
<210> SEQ ID NO 13
<211> LENGTH: 21
<212> TYPE: DNA
<213> ORGANISM: Artificial sequence
<220> FEATURE:
<223> OTHER INFORMATION: HBV probe
<220> FEATURE:
<221> NAME/KEY: misc_binding
<222> LOCATION: (1)..(21)

<400> SEQUENCE: 13
aagccaccca aggcacagct t                                              21

<210> SEQ ID NO 14
<211> LENGTH: 25
<212> TYPE: DNA
<213> ORGANISM: Artificial sequence
<220> FEATURE:
<223> OTHER INFORMATION: HCV probe
<220> FEATURE:
<221> NAME/KEY: misc_binding
<222> LOCATION: (1)..(25)

<400> SEQUENCE: 14
cgagtagtgt tgggtcgcga aaggc                                          25

<210> SEQ ID NO 15
<211> LENGTH: 30
<212> TYPE: DNA
<213> ORGANISM: Artificial sequence
<220> FEATURE:
<223> OTHER INFORMATION: HIV probe
<220> FEATURE:
<221> NAME/KEY: misc_binding
<222> LOCATION: (1)..(30)

<400> SEQUENCE: 15
tttttttttt gtcacacaac agatgggcac                                     30
```

What is claimed is:

1. A method for identifying HBV (Hepatitis type B Virus), HCV (Hepatitis type C Virus), and HIV (Human Immunodeficiency Virus) simultaneously comprising:
   (a) amplifying DNA fragments of the said viruses synchronously in a sample using different outer and inner primer sets for each virus; the outer primer sets consisting of SEQ ID NO:1 and SEQ ID NO:2 for HBV, SEQ ID NO:3 and SEQ ID NO:4 for HCV, SEQ ID NO:5 and SEQ ID NO:6 for HIV; the inner primer sets consisting of SEQ ID NO:7 and SEQ ID NO:8 for HBV, SEQ ID NO:9 and SEQ ID NO:10 for HCV, and SEQ ID NO:11 and SEQ ID NO:12 for HIV;
   (b) hybridizing the amplified fragments with different specific probes for identifying amplified DNA fragments from HBV, HCV, and HIV, the probes consisting of SEQ ID NO:13 for HBV, SEQ ID NO:14 for HCV, and SEQ ID NO:15 for HIV; and
   (c) detecting the hybrid products of (b).

2. A probe set for identifying amplified DNA fragments from HBV, HCV, and HIV, which consists of SEQ ID NO:13 for HBV, SEQ ID NO:14 for HCV, and SEQ ID NO:15 for HIV.

3. The probe set as claimed in claim 2, wherein each of the probes are labeled with a microsphere particle.

4. A kit for detecting HBV, HCV, and HIV comprising:
   (a) outer primer sets used to amplify DNA of a sample consisting of SEQ ID NO:1 and SEQ ID NO:2 for HBV; SEQ ID NO:3 and SEQ ID NO:4 for HCV; SEQ ID NO:5 and SEQ ID NO:6 for HIV;
   (b) inner primer sets used to amplify DNA of a sample consisting of SEQ ID NO: 7 and SEQ ID NO: 8 for HBV; SEQ ID NO: 9 and SEQ ID NO: 10 for HCV; SEQ ID NO: 11 and SEQ ID NO: 12 for HIV; and
   (c) probes used to identify the amplified DNA fragment comprising SEQ ID NO: 13 for HBV, SEQ ID NO: 14 for HCV and SEQ ID NO: 15 for HIV.

5. The kit as claimed in claim 4, wherein the inner primer sets are labeled with bioactive components.

6. The kit as claimed in claim 5, wherein the components are biotin.

7. The kit as claimed in claim 4, wherein the probes are labeled with a microsphere particle.

8. The kit as claimed in claim 4, further comprising a polymerase enzyme.

9. The kit as claimed in claim 4, further comprising a hybridization buffer.

10. The kit as claimed in claim 8, further comprising a substrate of an enzyme for a quantitation of a probe-amplified DNA complex.

* * * * *